US00PP21707P2

(12) United States Plant Patent
Oudolf

(10) Patent No.: US PP21,707 P2
(45) Date of Patent: Feb. 8, 2011

(54) ***SALVIA* PLANT NAMED 'ENDLESS LOVE'**
(50) Latin Name: ***Salvia* hybrid**
Varietal Denomination: Endless Love

(75) Inventor: Petrus Henricus Oudolf, Hummelo (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 12/587,114

(22) Filed: Oct. 1, 2009

(51) Int. Cl.
*A01H 5/00* (2006.01)

(52) U.S. Cl. ..... Plt./475
(58) Field of Classification Search ..... Plt./263, Plt./475

See application file for complete search history.

*Primary Examiner*—Susan B McCormick Ewoldt
(74) *Attorney, Agent, or Firm*—C. A. Whealy

(57) ABSTRACT

A new and distinct cultivar of *Salvia* plant named 'Endless Love', characterized by its compact, upright and outwardly spreading plant habit; strong and vigorous growth habit; freely flowering habit; and violet blue- colored flowers.

2 Drawing Sheets

Botanical designation: *Salvia* hybrid.
Cultivar denomination: 'ENDLESS LOVE'.

BACKGROUND OF THE INVENTION

The present invention relates to a new and distinct cultivar of *Salvia* plant, botanically known as *Salvia* hybrid and hereinafter referred to by the name 'Endless Love'.

The new *Salvia* plant originated from an open-pollination during the summer of 2006 of *Salvia verticillata* 'Purple Rain', not patented, as the female, or seed, parent with an unknown selection of *Salvia*, as the male, or pollen, parent. The new *Salvia* plant was discovered and selected by the Inventor as a single flowering plant from within the progeny of the stated open-pollination grown in a controlled environment in Hummelo, The Netherlands during the summer of 2007.

Asexual reproduction of the new *Salvia* plant by softwood cuttings in Hummelo, The Netherlands, since the summer of 2007, has shown that the unique features of this new *Salvia* plant are stable and reproduced true to type in successive generations.

SUMMARY OF THE INVENTION

Plants of the new *Salvia* have not been observed under all possible environmental conditions. The phenotype may vary somewhat with variations in environment such as temperature and light intensity without, however, any variance in genotype.

The following traits have been repeatedly observed and are determined to be the unique characteristics of 'Endless Love'. These characteristics in combination distinguish 'Endless Love' as a new and distinct cultivar of *Salvia:*

1. Compact, upright and outwardly spreading plant habit.
2. Strong and vigorous growth habit.
3. Freely flowering habit.
4. Violet blue-colored flowers.

Plants of the new *Salvia* can be compared to plants of the female parent, 'Purple Rain'. Plants of the new *Salvia* differ from plants of 'Purple Rain' in the following characteristics:

1. Plants of the new *Salvia* are more compact than plants of 'Purple Rain'.
2. Plants of the new *Salvia* are stronger than plants of 'Purple Rain'.
3. Plants of the new *Salvia* and 'Purple Rain' differ in flower color as plants of 'Purple Rain' have purple-colored flowers.

Plants of the new *Salvia* can be compared to plants of 'Rhapsody in Blue', disclosed in U.S. Plant Pat. No. 15,148. In side-by-side comparisons, plants of the new *Salvia* differed from plants of 'Rhapsody in Blue' in the following characteristics:

1. Plants of the new *Salvia* were more compact than plants of 'Rhapsody in Blue'.
2. Plants of the new *Salvia* and 'Rhapsody in Blue' differed in flower color.

BRIEF DESCRIPTION OF THE PHOTOGRAPHS

The accompanying colored photographs illustrate the overall appearance of the new *Salvia* plant, showing the colors as true as it is reasonably possible to obtain in colored reproductions of this type. Colors in the photographs may differ slightly from the color values cited in the detailed botanical description which accurately describe the actual colors of the new *Salvia* plant.

The photograph on the first sheet comprises a side perspective view of typical flowering plants of 'Endless Love' grown in an outdoor nursery.

The photograph at the top of the second sheet is a close-up view of a typical inflorescence of 'Endless Love'.

The photograph at the bottom of the sheet is a close-up view of the upper surface of a typical leaf of 'Endless Love'.

DETAILED BOTANICAL DESCRIPTION

Plants used for the aforementioned photographs and following description were grown under conditions which closely approximate commercial production conditions during October in an outdoor nursery in Lisserbroek, The Netherlands. During the production of the plants, day temperatures ranged from 12° C. to 22° C. and night temperatures ranged from 1° C. to 12° C. Plants were one year old when the photographs and description were taken. In the following description, color references are made to The Royal Horticultural Society Colour Chart, 2007 Edition, except where general terms of ordinary dictionary significance are used.

Botanical classification: *Salvia hybrida* 'Endless Love'.

Parentage:

*Female, or seed, parent.*—*Salvia verticillata* 'Purple Rain', not patented.

*Male, or pollen, parent.*—Unknown selection of *Salvia*, not patented.

Propagation:

*Type.*—By softwood cuttings.

*Time to produce a rooted young plant.*—About two months at 16° to 22° C.

*Root description.*—Main roots, fine; lateral roots, fine; white to dark brown in color; moderately dense.

Plant description:

*Type.*—Herbaceous perennial.

*Form.*—Upright and outwardly spreading plant form; uniform broad inverted triangle; flowers arranged in upright verticillasters on spikes.

*Branching habit.*—Freely basal branching with plants developing about 27 flowering stems.

*Growth habit.*—Moderately vigorous.

*Plant height.*—About 54.1 cm.

*Plant width.*—About 51 cm.

*Lateral branch description.*—Length: About 26.8 cm. Diameter: About 4 mm. Internode length: About 6.3 cm. Strength: Strong. Aspect: Mostly upright. Texture: Densely pubescent. Color: Close to 144C tinged with close to 178A to 178B.

Foliage description:

*Arrangement.*—Opposite, simple.

*Length.*—About 10.2 cm.

*Width.*—About 7.6 cm.

*Shape.*—Ovate.

*Apex.*—Broadly acute.

*Base.*—Cordate.

*Margin.*—Crenate to serrate.

*Texture, upper and lower surfaces.*—Densely pubescent; slightly rugose.

*Venation pattern.*—Pinnate.

*Color.*—Developing leaves, upper surface: Close to 144A. Developing leaves, lower surface: Close to 146B. Fully expanded leaves, upper surface: Close to 146A to 146B; venation, close to 148B. Fully expanded leaves, lower surface: Close to 147B to 147C; venation, close to 146D.

*Petiole length.*—About 4.2 mm.

*Petiole diameter.*—About 4 mm.

*Petiole texture, upper and lower surfaces.*—Pubescent.

*Petiole color, upper and lower surfaces.*—Close to 177A to 177B.

Flower description:

*Flower arrangement and shape.*—Single bilabiate flowers arranged in terminal verticillasters; flowers face mostly outwardly.

*Flowering habit.*—Freely flowering habit, about 180 flowers per inflorescence in about 22 whorls.

*Natural flowering season.*—Continuous flowering during the summer in The Netherlands; plants will reflower after removal of the flowers.

*Flower longevity on the plant.*—About five days; flowers not persistent.

*Fragrance.*—Not detected.

*Flower buds.*—Length: About 7 mm. Diameter: About 3.5 mm. Shape: Obovate. Color: Calyx, close to N77B to N77C; corolla, close to N89C.

*Inflorescence size.*—Length: About 22.5 cm. Diameter: About 2.5 cm.

*Flowers.*—Size: About 2 mm by 6 mm. Depth (height): About 1 cm.

*Petals.*—Arrangement: Two, fused at the base. Length, upper lip: About 8 mm. Length, lower lip: About 1.5 mm. Width, upper lip: About 6 mm. Width, lower lip: About 1.5 mm. Shape, upper lip: Broadly elliptic; apex, rounded to retuse; margin, entire. Shape, lower lip: Spatulate; apex, lobes obtuse; margin, entire. Texture, upper surface: Smooth, glabrous. Texture, lower surface: Sparsely pubescent. Color: Upper and lower lips, when opening and fully opened, upper surface: Close to 90B; towards the base, close to 90D. Upper and lower lips, when opening and fully opened, lower: Close to 90A; towards the base, close to 90D.

*Sepals.*—Arrangement: Five sepals fused into a tube. Length: About 7 mm. Width: About 1 mm. Shape: Narrowly elliptic. Apex: Acute. Margin: Entire. Texture, upper and lower surfaces: Pubescent. Color: Immature and mature, upper surface: Close to 148B. Immature and mature, lower surface: Close to N77B to N77C; stripes, close to N79C.

*Peduncles.*—Strength: Strong. Length: About 21.7 cm. Diameter: About 2.5 mm. Aspect: Erect to about 30° from vertical. Texture: Pubescent. Color: Close to 144C tinged with close to 178A to 178B; in between verticillasters, close to N79A.

*Pedicels.*—Strength: Strong. Length: About 4 mm. Diameter: About 0.75 mm. Aspect: About 30° from vertical. Texture: Pubescent. Color: Close to N79A.

*Reproductive organs.*—Stamens: Quantity per flower: Two; anthers dorsifixed. Filament length: About 0.1 mm. Filament color: Close to 90C. Anther shape: Broadly ovate. Anther length: About 0.5 mm. Anther color: Close to 199A to 199B. Pollen amount: Scarce. Pollen color: Close to 6A. Pistils: Quantity per flower: One. Pistil length: About 8 mm. Stigma shape: Cleft, two-parted. Stigma color: Close to 79A to 79B. Style length: About 6.5 mm. Style color: Close to N88A to N88D. Ovary color: Close to 145A.

*Seed/fruit.*—Seed and fruit production has not been observed.

Disease/pest resistance: Plants of the new *Salvia* have not been noted to be resistant to pathogens and pests common to *Salvia*.

Garden performance: Plants of the new *Salvia* have exhibited good tolerance to rain and wind and have been observed to be hardy to USDA Hardiness Zone 5 and to tolerate high temperatures of 30° C.

It is claimed:

1. A new and distinct *Salvia* plant named 'Endless Love' as illustrated and described.

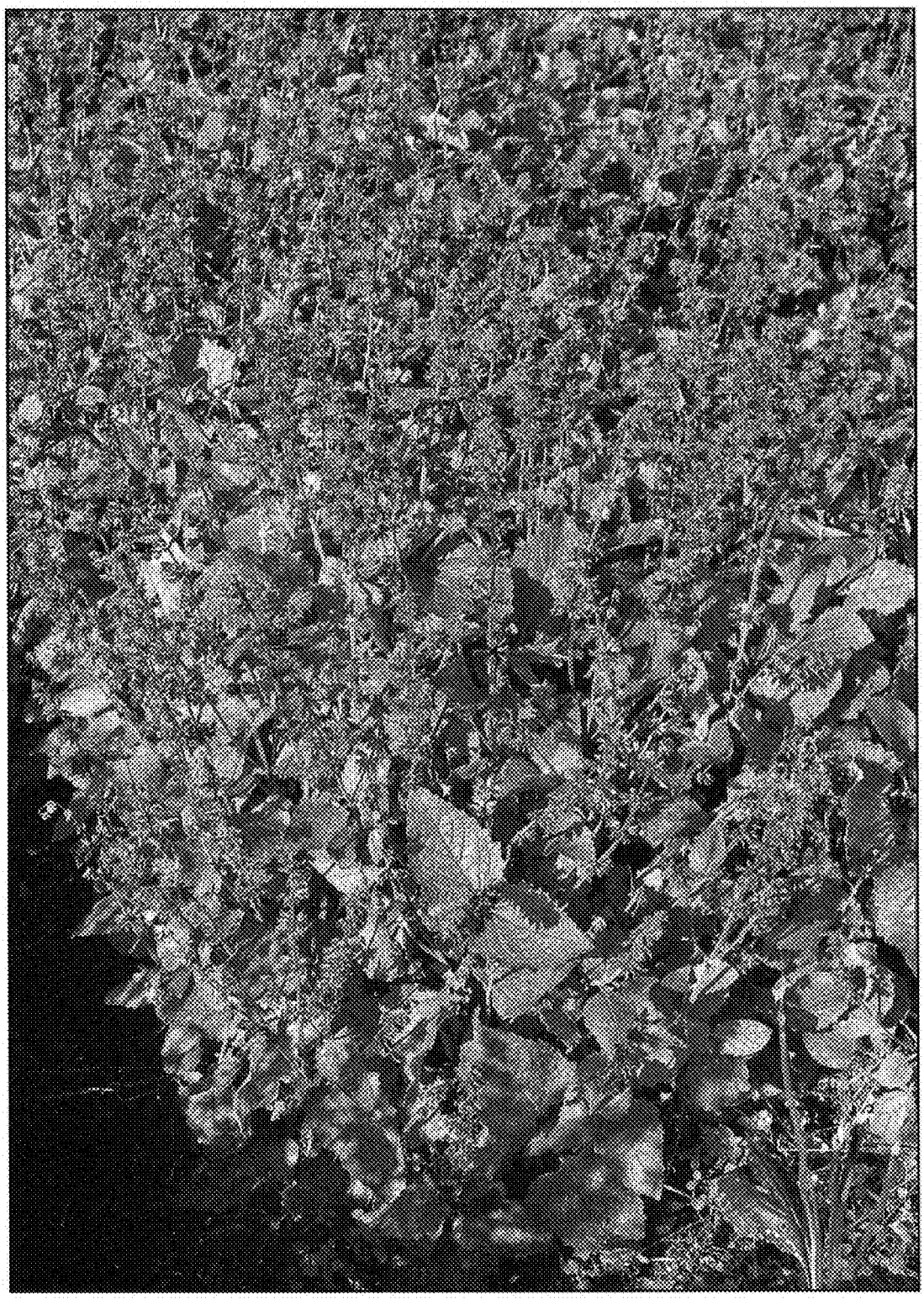

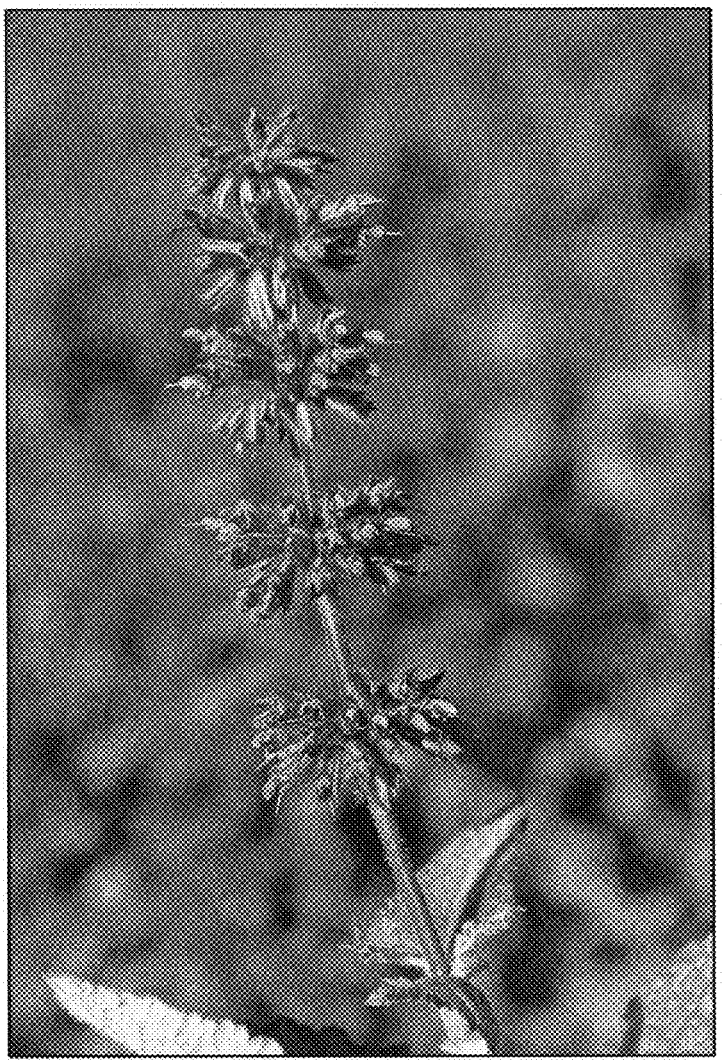
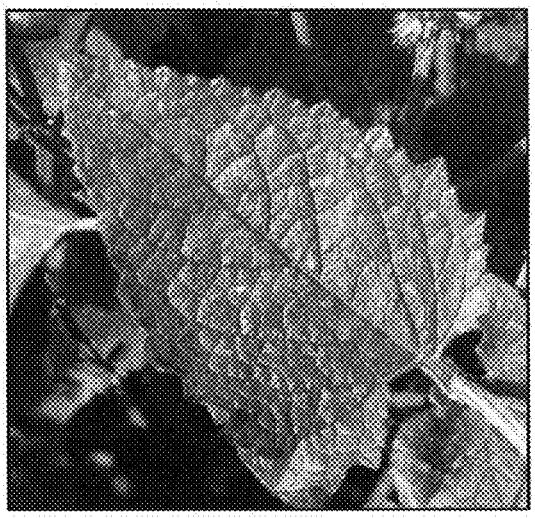

* * * * *